US00PP23375P3

(12) United States Plant Patent
Weber

(10) Patent No.: US PP23,375 P3
(45) Date of Patent: Feb. 5, 2013

(54) RASPBERRY PLANT NAMED 'CRIMSON GIANT'

(50) Latin Name: *Rubus idaeus* L.
Varietal Denomination: Crimson Giant

(75) Inventor: Courtney A. Weber, Geneva, NY (US)

(73) Assignee: Cornell University, Ithaca, NY (US)

( * ) Notice: Subject to any disclaimer, the term of this patent is extended or adjusted under 35 U.S.C. 154(b) by 22 days.

(21) Appl. No.: 12/932,475

(22) Filed: Feb. 25, 2011

(65) Prior Publication Data

US 2012/0222174 P1 Aug. 30, 2012

(51) Int. Cl.
*A01H 5/00* (2006.01)

(52) U.S. Cl. ..... Plt./204

(58) Field of Classification Search ..... Plt./204
See application file for complete search history.

*Primary Examiner* — Susan McCormick Ewoldt
(74) *Attorney, Agent, or Firm* — Harris Beach PLLC

(57) ABSTRACT

This invention relates to a new and distinct primocane bearing variety of red raspberry plant named 'Crimson Giant,' primarily adapted to growing conditions of west central New York and other regions of similar climate. 'Crimson Giant' is primarily characterized by sturdy upright canes growing primarily in a crown formation, very large conical fruit that is longer than broad, very late primocane production and bright red fruit color.

9 Drawing Sheets

STATEMENT REGARDING FEDERALLY SPONSORED RESEARCH OR DEVELOPMENT

Figure 1A:
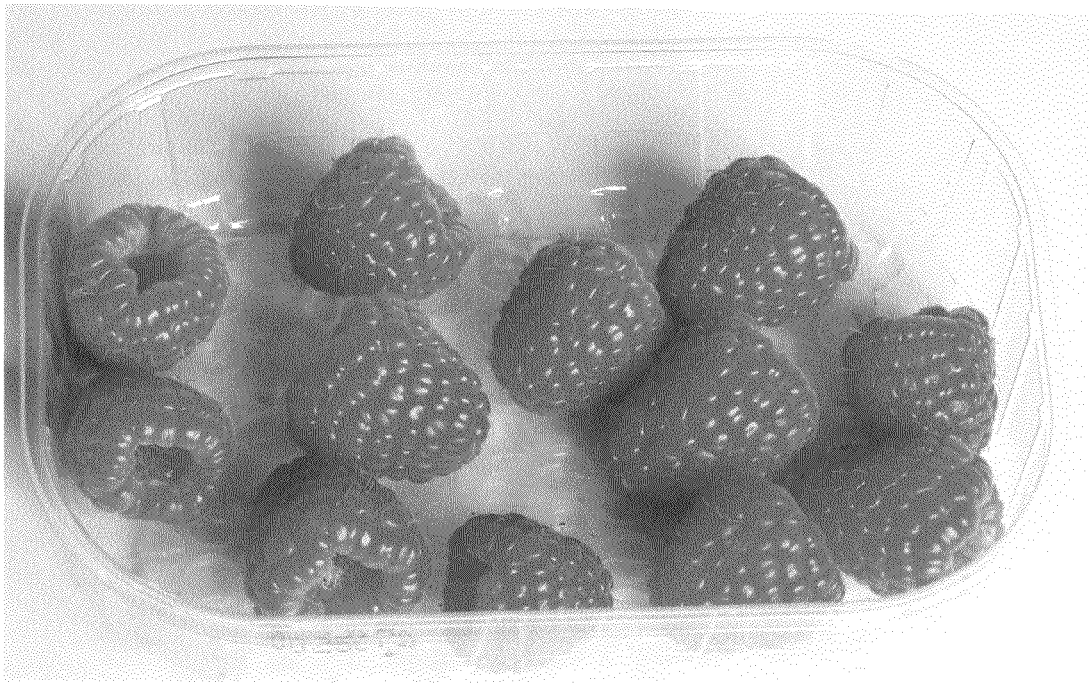

The disclosed invention was made with government support under contract no. NYG-632421 from the United States Department of Agriculture Hatch Funds. The government has rights in this invention.

1. Latin name of the genus and species of the plant claimed: *Rubus idaeus* L.
2. Variety denomination: Crimson Giant.

3. BACKGROUND OF THE INVENTION

The present invention relates to a new and distinct primocane bearing (fall bearing) red raspberry variety designated as 'Crimson Giant.' The variety is botanically known as *Rubus idaeus* L. The new and distinct variety of red raspberry originated from a hand-pollinated cross of the patented variety 'Titan' (patented as N.Y. 883, U.S. Plant Pat. No. 5,404) and Cornell selection NY950 (unpatented), which cross was made and the resulting seedling grown in Geneva, N.Y. The seedling, NY99-45, was selected from a controlled breeding plot in 1999. The new variety has been asexually propagated by dormant canes since 2000 and was established in tissue culture for propagation of plants for trials in 2006. This propagation has demonstrated that the combination of traits that characterize this variety are fixed and remain true to type through successive generations of asexual propagation. NY99-45 is being named and released as 'Crimson Giant' and is the subject of this invention.

4. SUMMARY OF THE INVENTION

'Crimson Giant' is primarily adapted to the climate and growing conditions of west central New York and other regions of similar temperate climate. This climate allows for the development of strong upright primocanes fruiting in the late fall season from September to November. 'Crimson Giant' benefits from the use of protective structures such as plastic hoop houses or high tunnels which allow for the complete harvest of the fall crop when the risk of frost is prevalent.

The following traits have been repeatedly observed and are determined to be unique characteristics of 'Crimson Giant,' which in combination distinguish this raspberry plant as a new and distinct variety:

1. large fruit size;
2. late fruit harvest on primocanes;
3. sturdy upright canes;
4. production of canes primarily in a crown;
5. strong primocane pigmentation; and
6. light green emerging leaves with blushed margins.

'Crimson Giant' differs from its parents by combining the fruit size and shape and production of canes in a crown of the maternal parent 'Titan' with the late season primocane fruiting habit of paternal parent NY950. 'Titan' is a floricane fruiting variety with green primocanes that produce no fruit on current year's growth. NY950 produces small round fruit on less sturdy primocanes that sucker abundantly from the mother plant. 'Crimson Giant' is dissimilar to other primocane fruiting varieties currently grown in New York in 'Crimson Giant' fruits considerably later, has larger fruit and produces canes primarily in a crown. 'Crimson Giant' is most similar in fruiting season and cane stature to the unpatented variety 'Heritage' which has sturdy upright primocanes that are heavily pigmented with stout spines. The fruiting season of 'Crimson Giant' begins up to 14 days later than the variety 'Heritage,' which was previously considered the latest primocane fruiting variety for the region. The fruit of 'Crimson Giant' are most similar to the floricane fruit of the maternal parent 'Titan' which has very large, bright red fruit that are attached to a pink torus, longer than broad and have a clasping collar, which makes them difficult to pick until fully mature. In contrast, the fruit of 'Crimson Giant' have an open collar allowing them to be picked as early as the immature light pink stage and are broader than the fruit of 'Titan' though still conic in shape and are attached to an unpigmented torus. In comparison to the similar varieties 'Titan' and 'Heritage,' 'Crimson Giant' differs by the following combination of characteristics described in Table 1. Color terminology is based on The Royal Horticultural Society Colour Chart (2001 edition).

TABLE 1

| Characteristic | 'Crimson Giant' (NY99-45) | Titan' (PP5,404) | 'Heritage' |
|---|---|---|---|
| 1. Mature primocane color | Greyed-red 181A | Green 143C | Greyed-red 180B |
| 2. Fruit shape | Broad conical | Conical | Round |
| 3. Fruit length (mm) | 26 | 30 | 15 |
| 4. Fruit width (mm) | 22 | 12 | 14 |
| 5. Fruit length × width ratio | 1.2 | 2.5 | 1.1 |
| 6. Mean fruit weight | 4.3 g | 3.9 g | 1.7 |
| 7. Maximum fruit weight | 8.0 g | 6.0 g | 3.2 g |
| 8. Mature fruit color | Red 45A | Red 42A | Red 53A |
| 9. Canes per plant | 13 | 15 | 29 |
| 10. Fruiting laterals per primocane | 14 | 0 | 18 |

5. BRIEF DESCRIPTION OF THE DRAWINGS

The color photographs illustrate typical characteristics of the new variety 'Crimson Giant' and are as true to color as reasonably possible with photographic reproductions of this type. Color in the photographs may differ slightly from the color value cited in the detailed botanical description, which accurately describes the color of 'Crimson Giant.' The photographs of actively growing canes and fruit were taken in Geneva, N.Y. on canes 4-6 months old as well as dormant winter canes prior to spring pruning.

FIG. 1A. Typical 'Crimson Giant' fruit shape and size in clamshell.

Figure 1B:
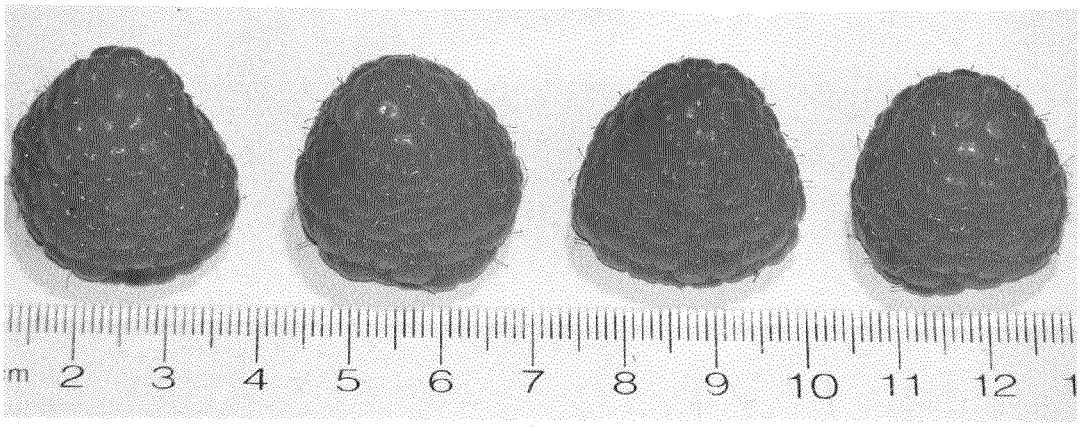

FIG. 1B. 'Crimson Giant' fruit top view.

Figure 1C:
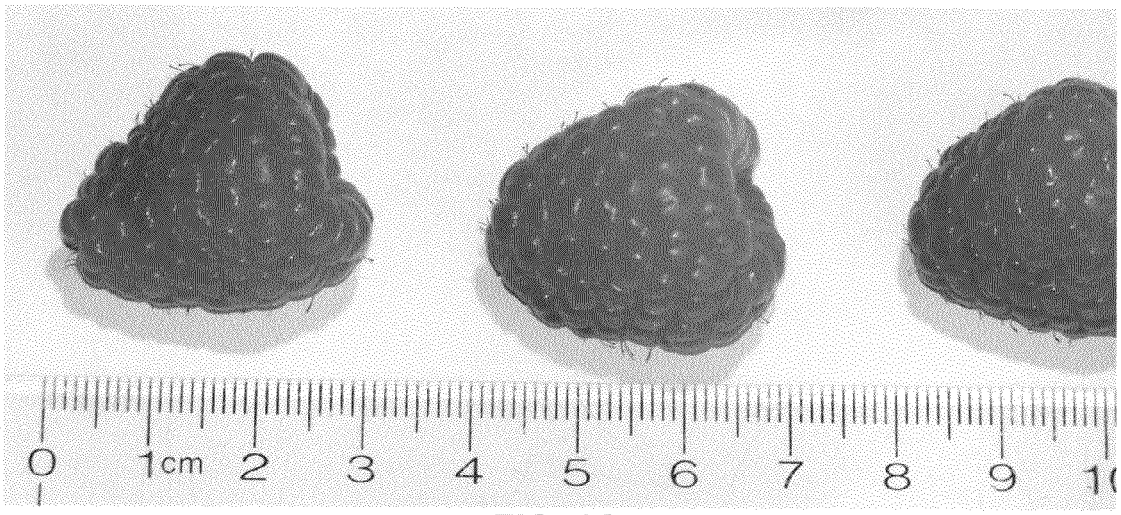

FIG. 1C. 'Crimson Giant' fruit side view.

Figure 2:
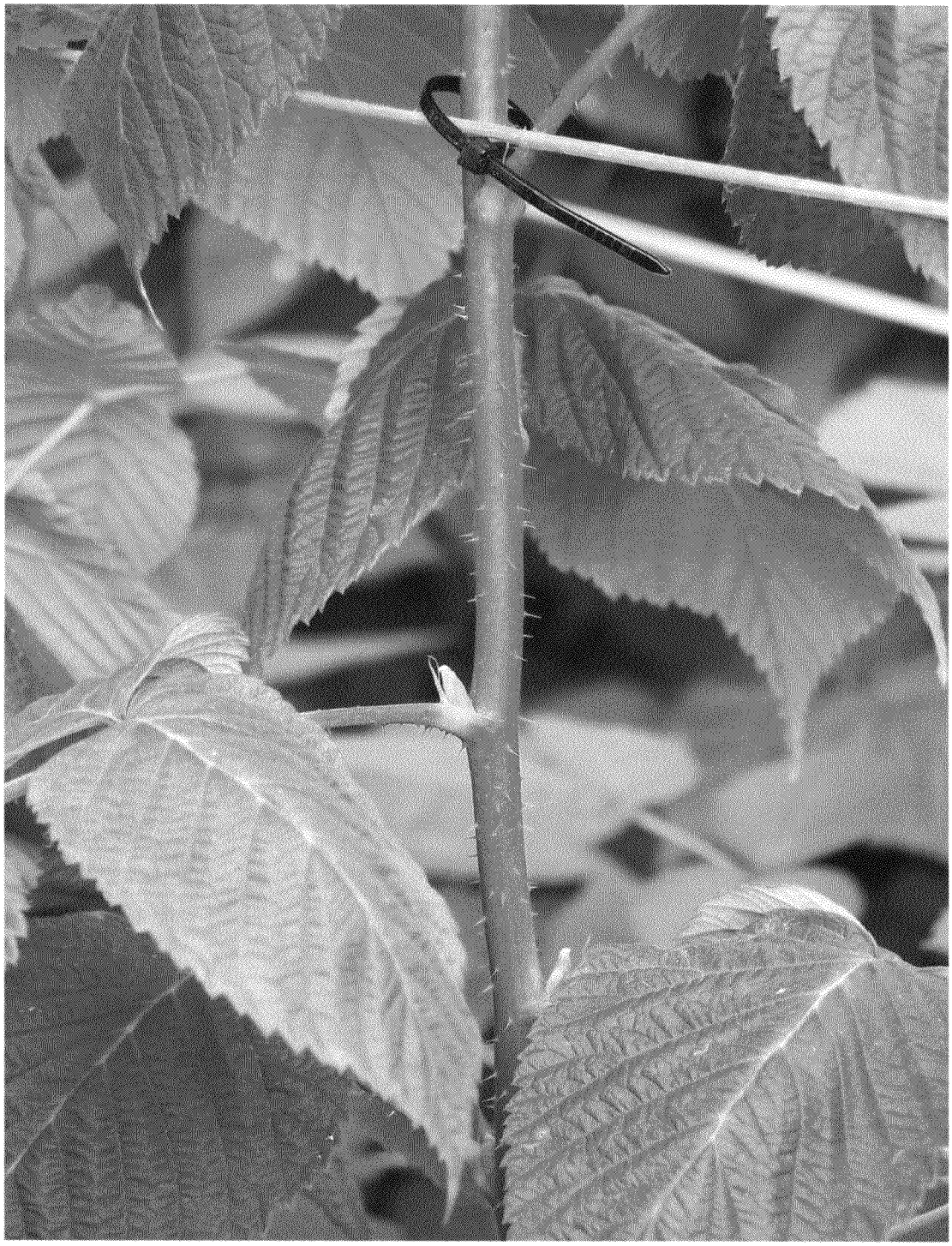

FIG. 2. Typical 'Crimson Giant' primocane pigmentation.

Figure 3A:
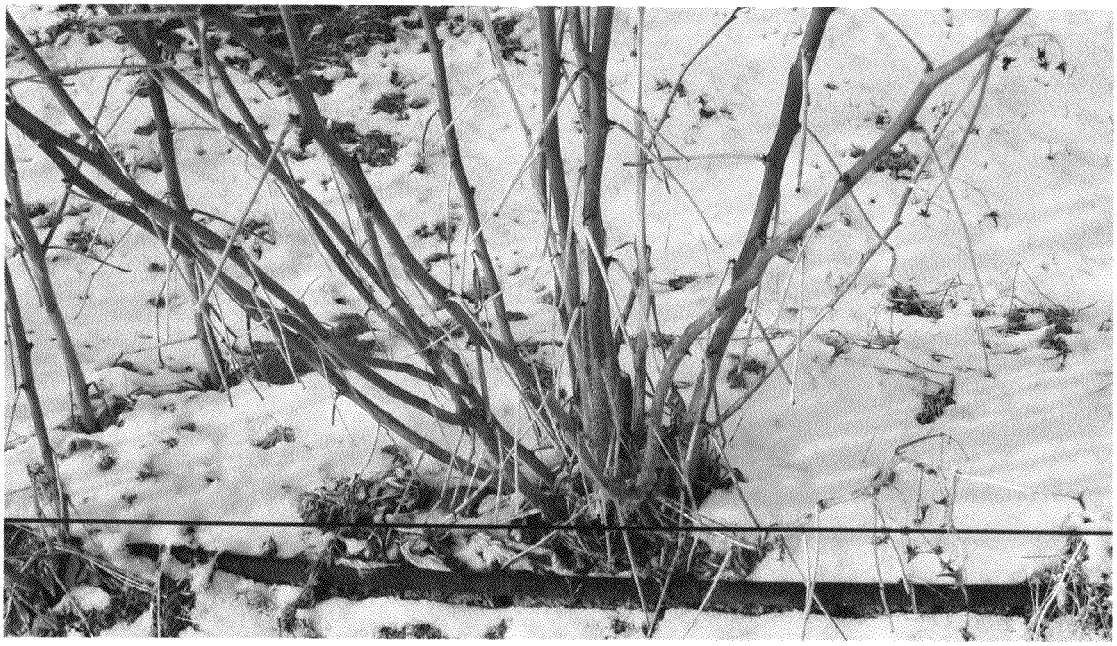

FIG. 3A. Typical 'Crimson Giant' cane configuration.

Figure 3B:
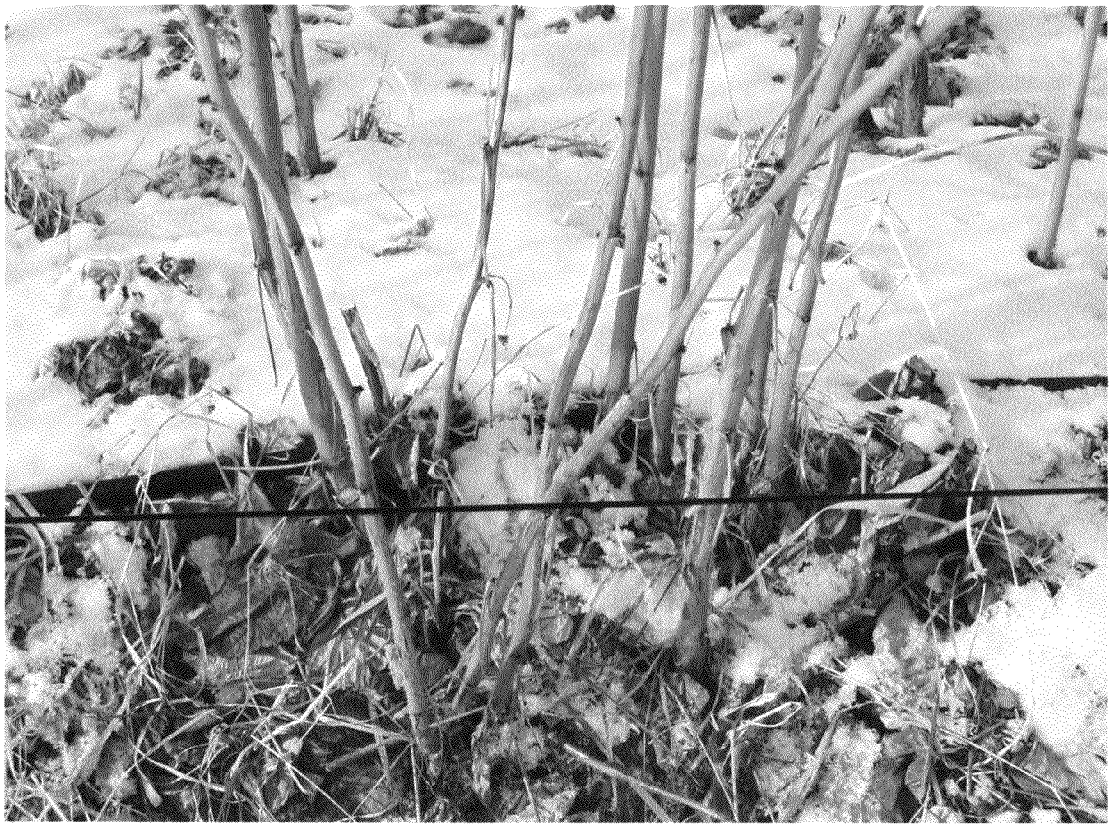

FIG. 3B. Typical 'Titan' cane configuration.

Figure 3C:
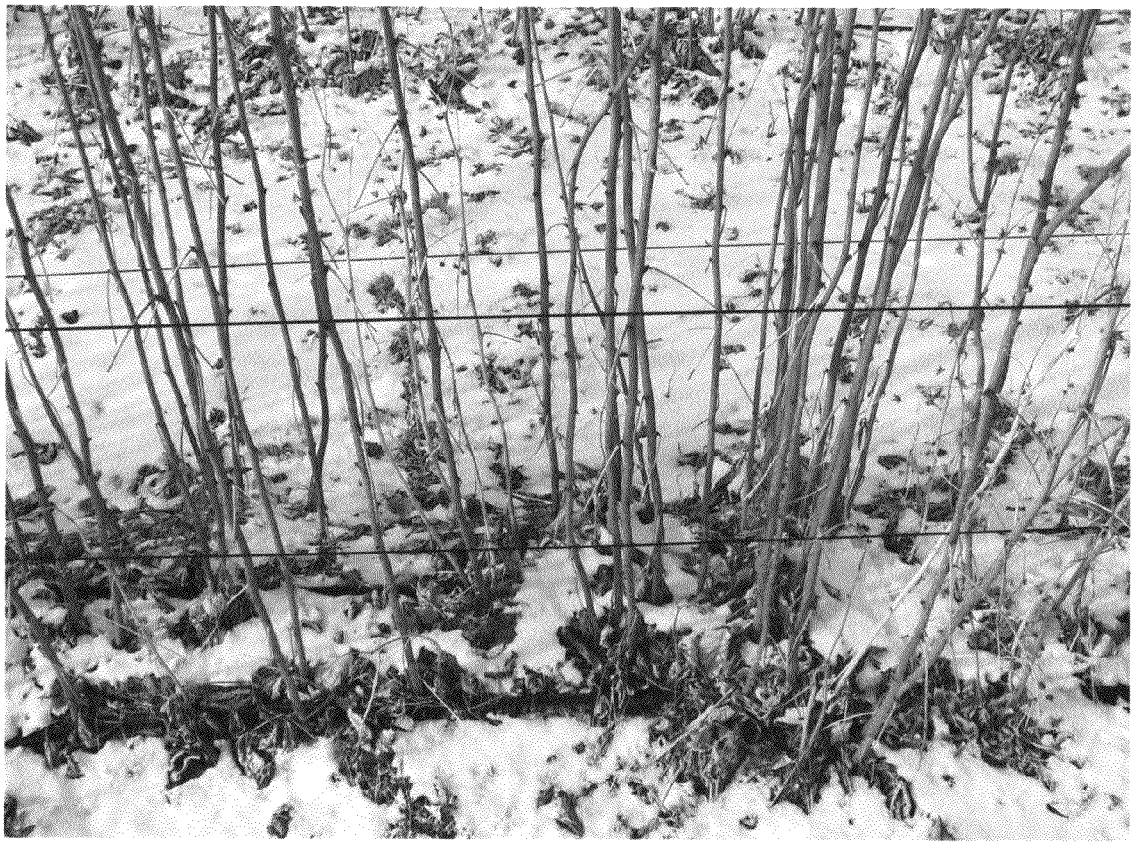

FIG. 3C. Typical 'Heritage' cane configuration.

Figure 4A:
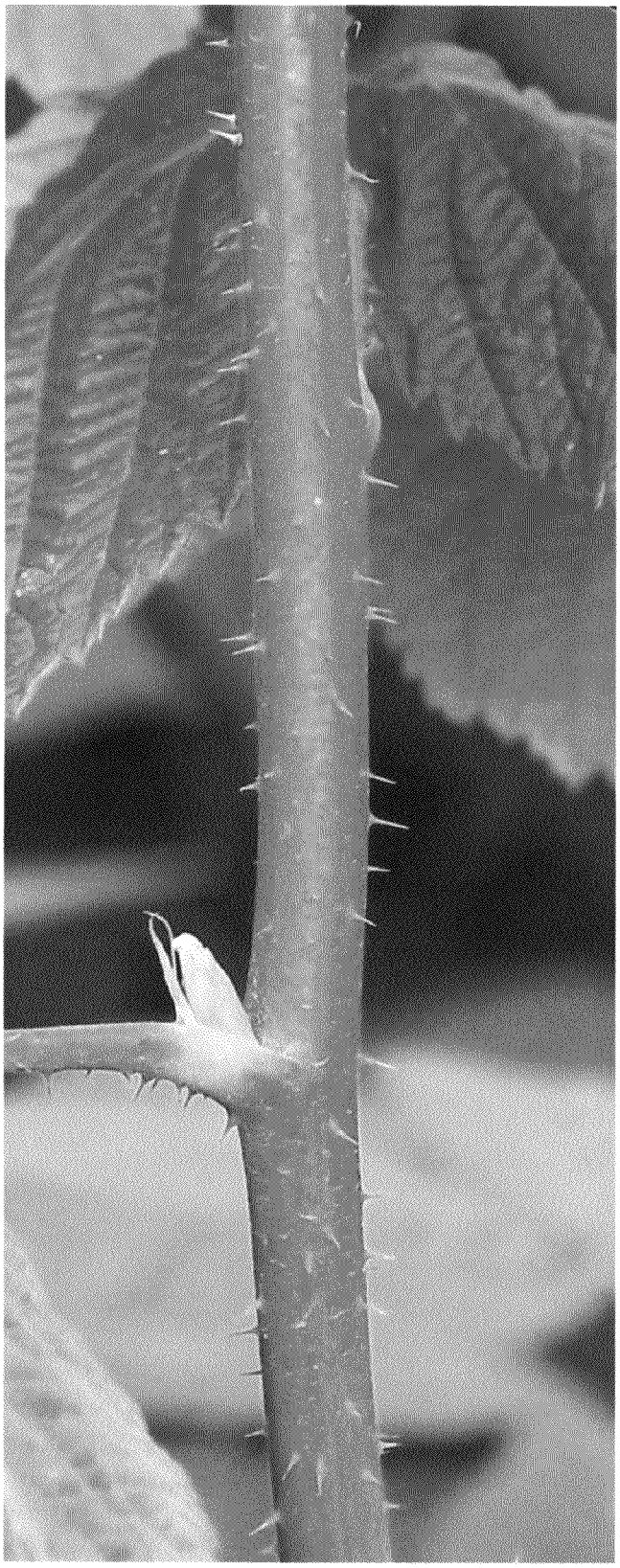

FIG. 4A. Typical 'Crimson Giant' spine development in center third of fruiting primocanes.

Figure 4B:
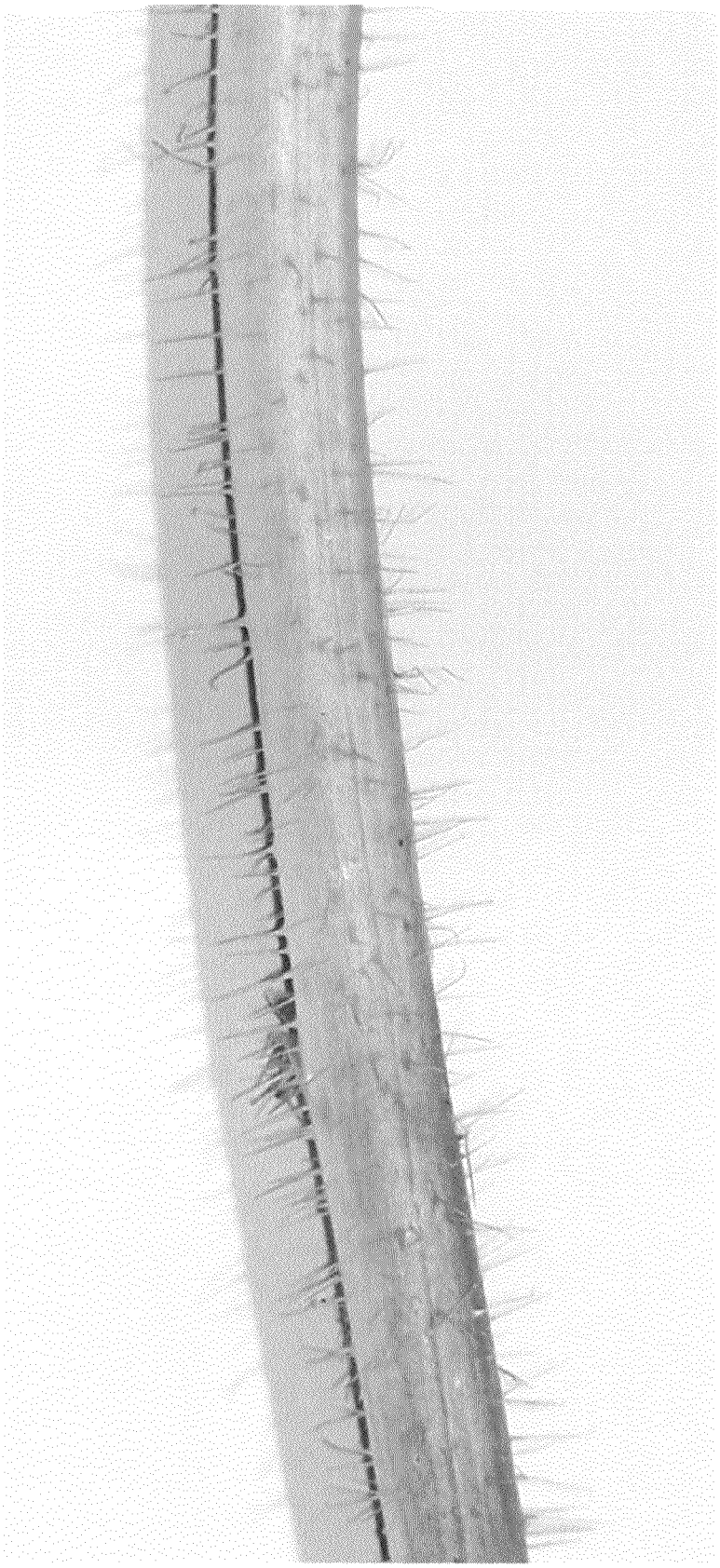

FIG. 4B. Typical 'Crimson Giant' spine development at the base of immature canes.

Figure 5:
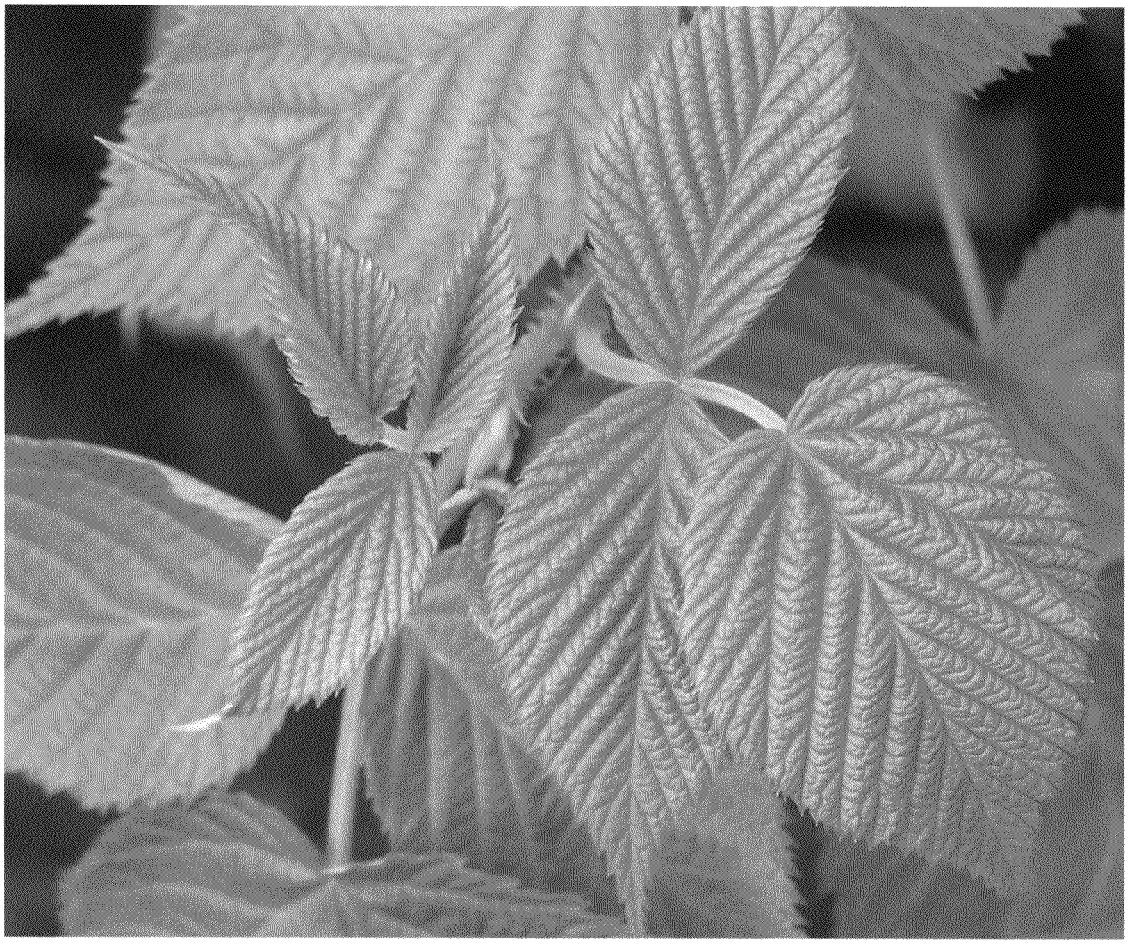

FIG. 5. Newly emerged 'Crimson Giant' leaves with light pigmentation on margin of the leaves.

6. DETAILED BOTANICAL DESCRIPTION

'Crimson Giant' has not been observed under all possible environmental conditions and as such the characteristics may vary in detail depending on weather conditions, day length, soil type and location.

The photographs together with the description of the new raspberry 'Crimson Giant' (NY99-45) are based upon the observations taken during the 2010 growing season in Geneva, N.Y. Measurements were taken on plants grown in a perennial planting in a high tunnel system that was planted in Geneva, N.Y. in 2009 with the canes emerging naturally in late April 2010. Flower measurements and characteristics were taken from secondary flowers and fruit measurements from secondary fruit. Mean measurements of fruit size were taken on 10 fruit samples throughout the season. Measurements of flower and fruit parts are means of 10 fruit samples. Cane measurements taken at the within the center third of the cane unless otherwise noted.

Classification:

*Family*.—Rosaceae.

*Botanical*.—*Rubus idaeus* L.

*Common name*.—Red Raspberry.

Parentage: 'Titan' (N.Y.883 U.S. Plant Pat. No. 5,404)× NY950 (unpatented).

Plant:

*Propagated*.—Asexual dormant canes, tissue culture.

Primocanes:

*Cane color*.—Mature — Greyed-red 181A. immature — Yellow-green 144B.

*Spines*.—Present.

*Cane length*.—1.7 m-2.1 m; mean 1.9 m.

*Cane diameter*.—7.5-9 mm; mean 8 mm.

*Internode length*.—3.5-5 cm; mean 4.25 cm.

*Number of fruiting lateral branches*.—13-19; mean 15.

*Maximum fruiting lateral length*.—32 cm.

*Pubescence*.—None.

Floricanes:

*Dormant color*.—Greyed-orange 165B; lateral branches greyed-orange 164B.

Spines:

*Density*.—High at base, moderate at middle third.

*Form*.—Moderately stout.

*Length*.—Mean 3 mm.

*Apex*.—Straight.

*Color*.—Yellow-green 144B on immature canes. Greyed-red 181A on mature canes.

Leaves:

*Type*.—Compound; primarily 3 leaflets; less than 5% 5 leaflets.

*Mature leaflet color*.—Upper surface Green 137A; lower surface Greyed-green 191B.

*Newly emerged leaflet color*.—Yellow-green 144A with slight blush of Greyed-red181A along the margins.

*Arrangement*.—Free.

*Terminal leaflet length*.—12.5-17.2 cm; mean 14.75 cm.

*Terminal leaflet width*.—9.6-12.1 cm; mean 10.75 cm.

*Terminal leaflet length to width ratio*.—1.4.

*Basal leaflet length*.—8.2-12.8 cm; mean 10.7 cm.

*Basal leaflet width*.—6-7.6 cm; mean 6.9 cm.

*Basal leaflet length to width ratio*.—1.6.

*Leaflet shape*.—Ovate.

*Terminal leaflet tip*.—Cuspidate.

*Basal leaflet tip*.—Auriculate.

*Leaflet margins*.—Doubly serrate.

*Terminal leaflet number of serrations*.—76.

*Basal leaf attachment*.—Flush.

*Leaflet overlap*.—None.

*Petiole length*.—6.6 cm.

*Petiole width*.—3 cm.

*Petiole spines*.—Present.

*Petiole spine apex*.—Straight.

Stipules:

*Quantity per leaf*.—2.

*Shape*.—Straight and erect.

*Length*.—8-9.5 mm; mean 8.5 mm.

*Color*.—Yellow-green 144B background with blush of Greyed-red 181A.

Flowers:

*Diameter*.—2-2.5 cm; mean 2.3 cm.

*Bud shape*.—Conical.

*Fragrance*.—None.

*Petals number*.—Primarily 5; less than 10% with 6.

*Petal shape*.—Obovate.
*Petal length*.—6-7.5 mm; mean 6.6 mm.
*Petal width*.—2-3.5 mm; mean 3 mm.
*Petal length to width ratio*.—2.2.
*Petal color*.—White 155C.
*Sepal number*.—Primarily 5; less than 10% with 6.
*Sepal length*.—7.5-10 mm; mean 9.2 mm.
*Sepal color*.—Upper surface Greyed-green 193A; lower surface Green 143C.
*Mean stigma number*.—94.
*Stigma color*.—White 155B.
*Mean stamen number*.—90.
*Anther color*.—White 155A.
*Anther filament color*.—White 155D.
*Stamen height*.—Below stigmatic surface.

Fruit:
*Shape*.—Broad conic.
*Fruit length*.—2.4-2.8 cm; mean 2.6 cm.
*Fruit width*.—2.1-2.4 cm; mean 2.2 cm.
*Fruit length to width ratio*.—1.2.
*Weight*.—4-8 g; mean 4.3 g.
*Number of drupelets*.—99.
*Color of mature fruit*.—Red 45A and later Red 46A.
*Pedicel diameter*.—1 mm.
*Pedicel color*.—Yellow-green 150B.
*Pedicel spines*.—Present; curved back towards cane.
*Adherence to receptacle*.—Light.

What is claimed is:

1. A new and distinct *Rubus idaeus* L. red raspberry plant named 'Crimson Giant' as described and illustrated herein.

* * * * *